US012774450B2

(12) United States Patent
Kaneko et al.

(10) Patent No.: US 12,774,450 B2
(45) Date of Patent: Oct. 27, 2026

(54) T CELL PROGENITOR PRODUCTION METHOD

(71) Applicants: Kyoto University, Kyoto (JP); TAKEDA PHARMACEUTICAL COMPANY LIMITED, Osaka (JP)

(72) Inventors: Shin Kaneko, Kyoto (JP); Shoichi Iriguchi, Kyoto (JP)

(73) Assignees: Kyoto University, Kyoto (JP); Takeda Pharmaceutical Company Limited, Osaka (JP)

( * ) Notice: Subject to any disclaimer, the term of this patent is extended or adjusted under 35 U.S.C. 154(b) by 854 days.

(21) Appl. No.: 17/915,940

(22) PCT Filed: Mar. 30, 2021

(86) PCT No.: PCT/JP2021/013465
§ 371 (c)(1),
(2) Date: Sep. 29, 2022

(87) PCT Pub. No.: WO2021/200901
PCT Pub. Date: Oct. 7, 2021

(65) Prior Publication Data

US 2023/0159891 A1 May 25, 2023

(30) Foreign Application Priority Data

Mar. 31, 2020 (JP) ................................ 2020-062512

(51) Int. Cl.
*C12N 5/0783* (2010.01)
*A61K 40/11* (2025.01)
*A61K 40/40* (2025.01)

(52) U.S. Cl.
CPC ............ *C12N 5/0636* (2013.01); *A61K 40/11* (2025.01); *A61K 40/40* (2025.01); *C12N 2500/02* (2013.01); *C12N 2501/115* (2013.01); *C12N 2501/155* (2013.01); *C12N 2501/165* (2013.01); *C12N 2501/2303* (2013.01); *C12N 2501/2306* (2013.01); *C12N 2501/2307* (2013.01); *C12N 2501/42* (2013.01); *C12N 2506/45* (2013.01)

(58) Field of Classification Search
None
See application file for complete search history.

(56) References Cited

FOREIGN PATENT DOCUMENTS

WO WO-2013/086436 A1 6/2013
WO WO-2018146297 A1 * 8/2018 ............ A61K 40/11
WO WO-2019067811 A1 * 4/2019 ............ A61K 35/28

OTHER PUBLICATIONS

Dougan, et al. GM-CSF, IL-3, and IL-5 family of cytokines: regulators of inflammation. Immunity. Apr. 2019; 50:796-811. (Year: 2019).*
To and Midwood. Plasma and cellular fibronectin: distinct and independent functions during tissue repair. Fibrogenesis and Tissue Repair. 2011. 4(21):1-17. (Year: 2011).*
D'Souza, et al. The many facets of Notch ligands. Oncogene. Sep. 2008. 27(38):5148-67. (Year: 2008).*
Piao, et al. Regulatory T cells condition lymphatic endothelia for enhanced transendothelial migration. Cell Reports. Jan. 2020. 30(4):1052-62. (Year: 2020).*
Razis and Noor. Naturally-occurring glucosinolates, glucoraphanin and glucoerucin are antagonists to aryl hydrocarbon receptor as their chemopreventive potency. (Year: 2015).*
Ditadi, et al. Human definitive haemogenic endothelium and arterial vascular endothelium represent distinct lineages. Nature Cell Biology. 2015; 17(5):580-591. (Year: 2015).*
Bari et al., "Expansion and Homing of Umbilical Cord Blood Hematopoietic Stem and Progenitor Cells for Clinical Transplantation," Biology of Blood and Marrow Transplantation, 2015, 21:1008-1019.
Jackson et al., "Targeting the aryl hydrocarbon receptor nuclear translocator complex with DMOG and Stemregenin 1 improved primitive hematopoietic stem cell expansion," Stem Cell Research, 2017, 21:124-131.
Stefanski et al., "Robust Progenitor T-Cell Production From Human Hematopoietic Progenitor Cell Expanded with Stemregenin-1," Biology of Blood and Marrow Transplantation, Mar. 1, 2018, 24:S358-S359, Abstract 519.
Boitano et al., "Aryl Hydrocarbon Receptor Antagonists Promote the Expansion of Human Hematopoietic Stem Cells," Science, Sep. 10, 2010, 329(10):1345-1348.
Ditadi et al., "Human definitive haemogenic endothelium and arterial vascular endothelium represent distinct lineages," Nature Cell Biology, Apr. 27, 2015, 17(5):580-591.
Reimann et al., "Human T-Lymphoid Progenitors Generated in a Feeder-Cell-Free Delta-Like-4 Culture System Promote T-Cell Reconstitution in NOD/SCID/$\gamma c^{-/-}$ Mice," Stem Cells, 2012, 30(8):1771-1780.
Singh et al., "Generation and function of progenitor T cells from StemRegenin-1-expanded CD34 human hematopoietic progenitor cells," Blood Advances, Oct. 22, 2019, 3(20):2934-2948.
Smith et al., "T cell progenitor therapy-facilitated thymopoiesis depends upon thymic input and continued thymic microenvironment interaction," JCI Insight, 2017, 2(10):e92056, 15 pages.
Ledran et al., "Efficient Hematopoietic Differentiation of Human Embryonic Stem Cells on Stromal Cells Derived from Hematopoietic Niches," Cell Stem Cell, Jul. 2008, 3:85-98.

(Continued)

*Primary Examiner* — Allison M Fox
*Assistant Examiner* — Gina Pronzati
(74) *Attorney, Agent, or Firm* — Foley & Lardner LLP

(57) ABSTRACT

The following are disclosed: a method for producing a T cell progenitor, including step (1) of culturing $CD34^+$ cell in a medium containing an aryl hydrocarbon receptor antagonist, a medium for T cell progenitor differentiation containing an aryl hydrocarbon receptor antagonist, and a T cell progenitor inducer containing an aryl hydrocarbon receptor antagonist.

5 Claims, 2 Drawing Sheets

(56) References Cited

OTHER PUBLICATIONS

Tao et al., “StemRegenin 1 selectively promotes expansion of Multipotent Hematopoietic Progenitors derived from Human Embryonic Stem Cells,” Journal of Stem Cells and Regenerative Medicine, 2017, 13(2):75-79.

* cited by examiner

T CELL PROGENITOR PRODUCTION METHOD

CROSS-REFERENCE TO RELATED APPLICATIONS

This application is the U.S. National Stage of PCT/JP2021/013465, filed Mar. 30, 2021, which claims priority to JP 2020-062512, filed Mar. 31, 2020.

TECHNICAL FIELD

The present invention relates to a method for producing a T cell progenitor, a medium for T cell progenitor differentiation, and a T cell progenitor inducer.

BACKGROUND OF INVENTION

Hematopoietic stem cell transplantation (HSCT) is a current standard treatment for many malignant and non-malignant hematopoietic diseases. Before infusion (transplant) of hematopoietic stem cells (HSC) (donor graft), the patient must undergo a pretreatment regimen, including chemotherapy or chemoradiotherapy. This pretreatment causes serious damage to the thymic microenvironment and thus delays the rearrangement of peripheral $CD4^+$ and $CD8^+$ T cells, making the patient vulnerable to opportunistic infections. The component of the thymic microenvironment most vulnerable to chemoradiotherapy is thymic epithelial cells, and the damage in thymic epithelial cells causes long-term impairment in thymus formation after transplantation.

For the problems with thymocytes development caused by the pretreatment, the therapy of infusing in vitro-derived T cell progenitors (proT) by transplanting hematopoietic stem cells is known to promote the recovery of the thymus damaged by exposure to irradiation. Aiming at recovering T cells damaged by thymic disorders after radiotherapy, the research and development of cell therapies (proT therapy) using T cell progenitors has been underway.

NPL 1 discloses that feeder-free systems based on immobilized Delta-like 4 (DLL4) can be used in differentiation into T cells, and that this method was used in allogeneic mouse models transplanted with hematopoietic stem cells to differentiate the cells into T cell progenitors and expand T cell progenitors, thereby increasing thymopoiesis.

NPL 2 discloses that $CD34^+$ umbilical cord blood cells were cultured in a plate coated with Delta-like-4 (DL-4) in a medium supplemented with IL-7, Flt3-ligand, a stem cell factor (SCF), and thrombopoietin, and that $CD34^-/CD7^-$ myeloid cells were excluded by FACS to obtain T cell progenitors.

NPL 3 discloses that $CD34^+/CD43^-/CD184^-/CD73^-$ haemogenic endothelia were cultured on OP-DLL4 stroma cells in a medium supplemented with TPO, Flt-3L, BMP4, IL11, SCF, and IL7 to obtain haematopoietic multipotent progenitors $CD45^+/RUNX1C^{hi}/MYB^{hi}/TAL1^{hi}/GATA2^{hi}$.

NPL 4 discloses that $CD34^+$ hematopoietic stem/progenitor cells (HSPC) were subjected to expansion culture and then co-cultured together with OP-DL1 cells in a medium supplemented with IL-7, Flt-3, and SCF to obtain T cell progenitors.

NPL 5 discloses that StemRegenin 1 (SR1), which is an aryl hydrocarbon receptor (AHR) antagonist, promoted expansion of $CD34^+$ cells, and that the AHR antagonist prevents the differentiation of hematopoietic stem cells to thereby promote NOD-SCID repopulating cell (SRC) numbers.

The practical application of proT therapies in the future will demand industrial methods for producing proT with high production efficiency (yield). However, there have been no reports on such production methods.

CITATION LIST

Non-Patent Literature

NPL 1: Smith et al., JCI Insight. 2017; 2 (10):e92056
NPL 2: Riemann et al., Stem Cells, 30 (8), 1771-1780, 2012
NPL 3: Ditadi et al., Nature Cell Biol., 17 (5), 580-591, 2015
NPL 4: Singh et al., Blood Advances, 3 (20), 2934-2948, 2019
NPL 5: Boitano et al., Science, 329 (10), 1345-1348, 2010

SUMMARY OF INVENTION

Technical Problem

An object of the present invention is to provide a method for producing a T cell progenitor that enables the production of a T cell progenitor with high efficiency, a medium for T cell progenitor differentiation, and a T cell progenitor inducer.

Solution to Problem

The present inventors conducted extensive research to achieve the object and found that T cell progenitor differentiation can be achieved with high efficiency by culturing $CD34^+$ cells (in particular, $CD34^+/CD43^-/CD184^-/CD73^-$ cells) in a medium supplemented with SR1, which is an aryl hydrocarbon receptor antagonist. The inventors also found that the medium is preferably further supplemented with RetroNectin, DLL4, and IL-3.

The present invention was completed by further research based on these findings and provides the following method for producing a T cell progenitor, medium for T cell progenitor differentiation, and T cell progenitor inducer.

[1] A method for producing a T cell progenitor, comprising step (1) of culturing a $CD34^+$ cell in a medium containing an aryl hydrocarbon receptor antagonist.

[2] The method according to [1], wherein the medium further contains at least one member selected from the group consisting of fibronectin, a fragment of fibronectin, Delta-like 4 (DLL4), and interleukin-3 (IL-3).

[2a] The method according to [1], wherein the culturing is performed in the presence of at least one member selected from the group consisting of fibronectin, a fragment of fibronectin, Delta-like 4 (DLL4), and interleukin-3 (IL-3).

[3] The method according to [1], wherein the medium further contains fibronectin and/or a fragment of fibronectin, and DLL4.

[3a] The method according to [1], wherein the culturing is performed in the presence of fibronectin and/or a fragment of fibronectin, and DLL4.

[4] The method according to [1], [3], or [3a], wherein the medium further contains IL-3.

[5] The method according to any one of [1] to [4], wherein the $CD34^+$ cell is a $CD34^-/CD43^-/CD184^-/CD73^-$ cell.

[5a] The method according to any one of [1] to [4], wherein the $CD34^{+}$ cell is a $CD34^{-}/CD7^{-}/CD43^{-}/CD184^{-}/CD73^{-}$ cell.

[6] The method according to any one of [1] to [5a], wherein the T cell progenitor is a T cell progenitor induced from a pluripotent stem cell.

[6a] The method according to any one of [1] to [5a], wherein the $CD34^{+}$ cell is induced from a pluripotent stem cell.

[6b] The method according to [6] or [6a], wherein the pluripotent stem cell is an induced pluripotent stem cell (iPS cell).

[7] The method according to any one of [1] to [6b], wherein the aryl hydrocarbon receptor antagonist is StemRegenin 1 (SR1).

[8] The method according to any one of [1] to [7], wherein the culturing is a culture in the absence of a feeder cell.

[8a] The method according to any one of [1] to [8], further comprising step (X) of preparing an iPS cell, wherein in step (1), a $CD34^{+}$ cell derived from the iPS cell is used.

[8b] The method according to any one of [1] to [8a], further comprising step (Y) of inducing differentiation of a pluripotent stem cell into a $CD34^{+}$ cell, wherein in step (1), the $CD34^{+}$ cell is used.

[8c] The method according to [8b], further comprising step (Z) of selecting a hemogenic endothelial cell (a $CD34^{+}/CD43^{-}/CD184^{-}/CD73^{-}$ cell) from $CD34^{+}$ cells obtained in step (Y).

[9] A medium for T cell progenitor differentiation, comprising an aryl hydrocarbon receptor antagonist.

[10] The medium according to [9], further comprising at least one member selected from the group consisting of fibronectin, a fragment of fibronectin, DLL4, and IL-3.

[11] The medium according to [9], further comprising fibronectin and/or a fragment of fibronectin, and DLL4.

[12] The medium according to [9] or [11], further comprising IL-3.

[13] The medium according to any one of [9] to [12], wherein the aryl hydrocarbon receptor antagonist is SR1.

[14] A T cell progenitor inducer comprising an aryl hydrocarbon receptor antagonist.

[15] The inducer according to [14], further comprising at least one member selected from the group consisting of fibronectin, a fragment of fibronectin, DLL4, and IL-3.

[16] The inducer according to [14], further comprising fibronectin and/or a fragment of fibronectin, and DLL4.

[17] The inducer according to [14] or [16], further comprising IL-3.

[18] The inducer according to any one of [14] to [17], wherein the aryl hydrocarbon receptor antagonist is SR1.

[19] A T cell progenitor obtained by the method of any one of [1] to [8c].

[20] A cell-transplant therapeutic agent comprising the T cell progenitor of [19].

[21] A kit for T cell progenitor differentiation, comprising an aryl hydrocarbon receptor antagonist.

[22] The kit according to [21], further comprising at least one member selected from the group consisting of fibronectin, a fragment of fibronectin, DLL4, and IL-3.

[23] The kit according to [21], further comprising fibronectin and/or a fragment of fibronectin, and DLL4.

[24] The kit according to [21] or [23], further comprising IL-3.

[25] The kit according to any one of [21] to [24], wherein the aryl hydrocarbon receptor antagonist is SR1.

Advantageous Effects of Invention

The present invention enables the production of T cell progenitors from $CD34^{+}$ cells with high efficiency.

DESCRIPTION OF EMBODIMENTS

Figure 1:
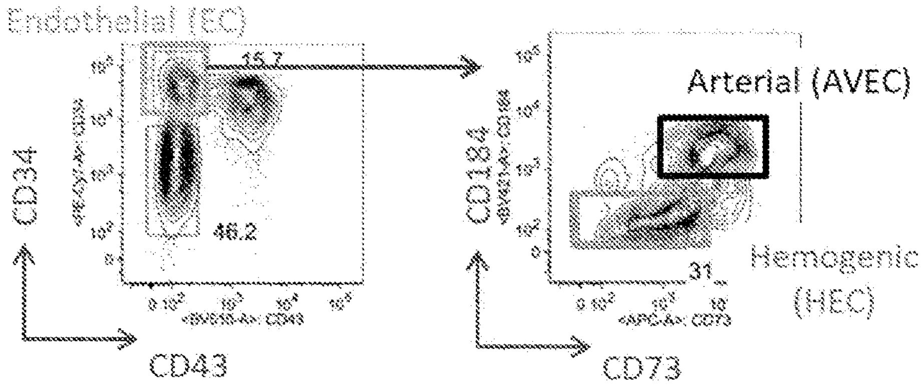
FIG. 1 shows the results of flow cytometry on an immunostained cell population containing $CD34^{+}$ cells differentiated from induced pluripotent stem cells.

Embodiments of the present invention are described below in detail.

In this specification, the term "comprise" also encompasses the meanings of both "consisting essentially of" and "consisting of."

In the present specification, the term "culture" refers to maintenance or/and proliferation of cells in an in vitro environment. The term "culturing" refers to maintaining or/and proliferating cells outside tissue or outside the body (e.g., in a cell culture dish or flask).

In this specification, the term "pluripotent stem cells" refers to embryonic stem cells (ES cells) and cells with pluripotency similar to that of ES cells, i.e., cells that have the potential to differentiate into various biological tissues (including all of endoderm, mesoderm, and ectoderm). Examples of cells with pluripotency similar to that of ES cells include induced pluripotent stem cells (which are sometimes referred to as "iPS cells" in this specification).

In the present specification, the term "cell population" refers to two or more cells of the same or different kind. The term "cell population" also refers to a mass of cells of the same or different kind.

In the present specification, the term "hematopoietic stem cells" refers to multipotent stem cells that can be differentiated into blood cells. Hematopoietic stem cells are present mainly in the bone marrow in the human body and differentiated into leucocytes (neutrophils, eosinophils, basophils, lymphocytes, monocytes, and macrophages), erythrocytes, platelets, mast cells, dendritic cells, etc. In the present invention, hematopoietic stem cells may be cells isolated from a biological tissue such as bone marrow, or cells derived from ES cells or iPS cells.

In the present specification, the term "hematopoietic progenitor cells" refers to cells that can be differentiated into cells such as lymphocytes, eosinophils, neutrophils, basophils, erythrocytes, or megakaryocytes. Hematopoietic progenitor cells can be recognized by their surface antigen CD34 and/or CD43 being positive.

In the present specification, the term "positive (+)" means that a protein or gene is expressed in levels detectable by methods known in the art. In the case of a protein that is expressed intracellularly and does not appear on the cell surface (e.g., a transcription factor or a subunit thereof), a reporter protein is expressed together with the protein, and the reporter protein is detected, whereby the target protein can be detected. Gene detection can be performed by using nucleic acid amplification and/or nucleic acid detection methods, such as RT-PCR, microarray, biochip, and RNA-Seq.

In the present specification, the term "negative (−)" means that the expression level of a protein or gene is below the lower limit of detection by all or any of the known methods as described above. The lower limit of detection of protein or gene expression may vary depending on the method. In the present specification, the term "cell surface marker" refers to a protein expressed on the cell surface that can be labeled (stained) with fluorescent substances and that facilitates the detection, condensation, isolation, or the like of cells expressing a cell marker. The cell marker refers to a gene that is expressed (positive marker) or not expressed (negative marker) specifically in a given cell type, and specifically a substance that is produced (positive marker) or not produced (negative marker) as mRNA by transcription of the gene in a genome or as a protein by translation of the mRNA.

Such cell surface markers can be detected by immunological assays using antibodies specific for the cell surface markers, such as ELISA, immunostaining, and flow cytometry.

In the present specification, the term "expression" is defined as the transcription and/or translation of a specific nucleotide sequence driven by an intracellular promoter.

In the present specification, "T cell progenitors" (proT) refer to hematopoietic cells produced in the process of differentiation from hematopoietic stem cells (HSCs) into CD3-positive T cells in a human living body, and are CD34-positive and CD7-positive ($CD34^+/CD7^+$ cells). Further, in the present specification, proT can be CD43-negative, CD1a-negative, and/or CD116-negative.

The $CD34^+$ cells for use in the present invention are not particularly limited and may be, for example, those induced in vitro according to known methods (e.g., $CD34^+$ cells obtained by inducing differentiation of hematopoietic progenitor cells (HPC) from pluripotent stem cells), or $CD34^+$ cells isolated from biological tissue by known methods.

$CD34^+$ cells can be produced by subjecting pluripotent stem cells to a known method. If the pluripotent stem cells are iPS cells, $CD34^+$ cells can be produced, for example, by inducing differentiation of hematopoietic progenitor cells according to the methods disclosed in WO2017/221975, WO2018/135646, or Cell Reports 2 (2012) 1722-1735.

The biological tissue from which $CD34^+$ cells are isolated can be any tissue containing $CD34^+$ cells, and can be, for example, bone marrow, umbilical cord blood, blood, or thymus.

The $CD34^+$ cells and pluripotent stem cells for use in the present invention are preferably cells certified by the Good Manufacturing Practice (GMP) standards from the standpoint of therapeutic applications.

Examples of pluripotent stem cells include embryonic stem cells (ES cells), induced pluripotent stem cells (iPS cells), embryonic carcinoma cells (EC cells), and embryonic germ stem cells (EG cells). The pluripotent stem cells are preferably iPS cells (more preferably human iPS cells). If the pluripotent stem cells are ES cells or any cells derived from a human embryo, those cells may be produced by destroying the embryo or without destroying the embryo, and are preferably produced without destroying the embryo.

For "ES cells," various mouse ES cell lines established by inGenious Targeting Laboratory, RIKEN (Institute of Physical and Chemical Research), and the like are available as mouse ES cells; and various human ES cell lines established by the University of Wisconsin, NIH, RIKEN, Kyoto University, the National Center for Child Health and Development, Cellartis, and the like are available as human ES cells. For example, human ES cell lines for use may be CHB-1 to CHB-12, RUES1, RUES2, HUES1 to HUES28, and other cell lines distributed by ESI Bio; H1, H9, and other cell lines distributed by WiCell Research Institute; and KhES-1, KhES-2, KhES-3, KhES-4, KhES-5, SSES1, SSES2, SSES3, and other cell lines distributed by RIKEN.

The term "induced pluripotent stem cells" refers to cells that are obtained by reprogramming mammalian somatic cells or undifferentiated stem cells by introducing specific factors (nuclear reprogramming factors). Various induced pluripotent stem cells are available at present. Usable induced pluripotent stem cells include iPS cells established by Yamanaka et al. by introducing four factors, Oct3/4, Sox2, Klf4, and c-Myc, into mouse fibroblasts (Takahashi K, Yamanaka S., Cell, (2006) 126: 663-676); iPS cells derived from human cells, established by introducing similar four factors into human fibroblasts (Takahashi K, Yamanaka S., et al. Cell, (2007) 131: 861-872); Nanog-iPS cells established by sorting cells using expression of Nanog as an indicator after introduction of the 4 factors (Okita, K., Ichisaka, T., and Yamanaka, S. (2007), Nature 448, 313-317); iPS cells produced by a method not using c-Myc (Nakagawa M, Yamanaka S., et al., Nature Biotechnology, (2008) 26, 101-106); and iPS cells established by introducing 6 factors by a virus-free method (Okita K et al., Nat. Methods 2011 May; 8 (5): 409-12, Okita K et al. Stem Cells. 31 (3): 458-66). It is also possible to use induced pluripotent stem cells established by Thomson et al. by introducing 4 factors OCT3/4, SOX2, NANOG, and LIN28 (Yu J., Thomson J A. et al., Science (2007) 318: 1917-1920); induced pluripotent stem cells produced by Daley et al. (Park I H, Daley G Q. et al., Nature (2007) 451: 141-146); induced pluripotent stem cells produced by Sakurada et al. (JP2008-307007A); and the like.

Additionally, usable induced pluripotent stem cells also include any induced pluripotent stem cells known in the art and disclosed in all published articles (e.g., Shi Y., Ding S., et al., Cell Stem Cell, (2008) Vol. 3, Issue 5, 568-574; Kim J B., Scholer H R., et al., Nature, (2008) 454, 646-650; Huangfu D., Melton, D A., et al., Nature Biotechnology, (2008) 26, No. 7, 795-797), as well as patent documents (e.g., JP2008-307007A, JP2008-283972A, US Patent Publication No. 2008/2336610, US Patent Publication No. 2009/047263, WO2007/069666, WO2008/118220, WO2008/124133, WO2008/151058, WO2009/006930, WO2009/006997, and WO 2009/007852).

Available induced pluripotent cell lines include various iPS cell lines established by NIH, RIKEN, Kyoto University, and the like. Examples of human iPS cell lines include HiPS-RIKEN-1A, HiPS-RIKEN-2A, HiPS-RIKEN-12A, and Nips-B2 from RIKEN; and Ff-I01s04, QHJI, RWMH, DRXT, RJWI, YZWJ, ILCL, GLKV, 253G1, 201B7, 409B2, 454E2, 606A1, 610B1, and 648A1 from Kyoto University.

The method for producing a T cell progenitor according to the present invention includes step (1) of culturing $CD34^+$ cells in a medium containing an aryl hydrocarbon receptor antagonist (which is sometimes referred to as a "medium for T cell progenitor differentiation" in this specification).

The medium for T cell progenitor differentiation contains a medium used in culturing animal cells as a basal medium, and contains an aryl hydrocarbon receptor antagonist. The basal medium can be any medium that can be used in culturing animal cells. Examples of basal mediums include IMDM, Medium 199, Eagle's Minimum Essential Medium (EMEM), αMEM, Dulbecco's Modified Eagle's Medium (DMEM), Ham's F12, RPMI 1640, Fischer's medium, MCDB 131, Neurobasal Medium (Life Technologies), StemSpan SFEM II (STEMCELL Technologies), and mixed mediums of these.

The aryl hydrocarbon receptor is a transcription factor that belongs to the Per-Arnt-Sim (PAS) family. The AHR is inactive when not bound to a ligand. When an aromatic hydrocarbon compound binds to the AHR as a ligand, the AHR translocates into the nucleus and forms a heterodimer with a molecule called "AhR nuclear translocator" (ARNT) in the nucleus. The heterodimer binds to a xenobiotic response element (XRE) on DNA to activate transcription. The aryl hydrocarbon receptor antagonist (AHR antagonist) refers to a substance that inhibits at least partly or entirely the reaction that occurs when an agonist binds to AHR. The AHR antagonist may be one that acts directly on AHR, or one that acts indirectly on AHR through action on another substance.

The aryl hydrocarbon receptor antagonist is not particularly limited and includes low-molecular compounds, high-molecular compounds, proteins such as antibodies and fragments of antibodies, peptides, and nucleic acids. Specifically, the aryl hydrocarbon receptor antagonist include SR1(4-(2-((2-(benzo[b]thiophen-3-yl)-9-isopropyl-9H-purin-6-yl)amino)ethyl)phenol), α-naphthoflavone, 1,4-dihydroxyanthraquinone, 1,5-dihydroxyanthraquinone, 1,8-dihydroxyanthraquinone, galangin, resveratrol, PD98059, CH-223191, GNF-351, TSU-16, 6,2',4'-trimethoxyflavone, 3',4'-dimethoxyflavone, and compounds disclosed as AHR antagonists in WO2012/015914. In particular, the aryl hydrocarbon receptor antagonist is preferably SR1.

The AHR antagonist in a medium can be of any concentration as long as T cell progenitors can be produced, and the concentration can be appropriately adjusted according to the type of the AHR antagonist for use. For example, if the AHR antagonist is SR1, the concentration of the AHR antagonist can be 0.1 nM to 300 nM, and preferably 0.1 nM to 100 nM.

The medium for T cell progenitor differentiation preferably further contains at least one member selected from the group consisting of fibronectin, a fragment of fibronectin, DLL4, and IL-3. The medium for T cell progenitor differentiation more preferably contains two or more members, and particularly preferably three members of the following: (i) fibronectin and/or a fragment of fibronectin, (ii) DLL4, and (iii) IL-3. The medium for T cell progenitor differentiation still more preferably contains fibronectin and/or a fragment of fibronectin and DLL4, and yet more preferably further contains IL-3.

The fragment of fibronectin (FN) is selected from the fragments contained in the FN-binding domain, cell adhesion domain, or heparin-binding domain. The fragment of fibronectin can be a fragment containing, for example, at least one fragment selected from $III_1$, $III_2$, $III_3$, $III_7$, $III_8$, $III_9$, $III_{11}$, $III_{12}$, $III_{13}$, and CS-1, and can also be a fragment of repeatedly linked multiple domains. The fragment of fibronectin for use can be, for example, a fragment containing a cell adhesion domain containing a ligand for VLA-5, a heparin-binding domain, CS-1 domain, which is a ligand for VLA-4, or $III_1$ etc. Additionally, examples of the fragment of fibronectin also include CH-271, CH-296, H-271, and H-296 disclosed in J. Biochem., Vol. 110, pp. 284-291 (1991), derivatives of these, and modified products of these. CH-296 is commercially available under the trade name of RetroNectin. The two-thirds of the polypeptide from the C-terminus of $III_1$ is also commercially available under the name of Fibronectin Fragment $III_1$-C.

FN and/or a fragment of FN for use may be immobilized on an appropriate solid phase, such as a cell culture vessel material or a cell culture carrier (e.g., beads, a membrane, or a glass slide). FN and/or a fragment of FN can be immobilized on a solid phase in accordance with the method disclosed in, for example, WO00/09168A. FN and/or a fragment of FN in a medium can be of any concentration as long as T cell progenitors can be produced. For example, the concentration of FN and/or a fragment of FN is preferably 0.001 μg/mL to 500 μg/mL, and more preferably 0.01 μg/mL to 500 μg/mL. If FN and/or a fragment of FN is immobilized for use, immobilization on a solid phase can be performed by using a solution of FN and/or a fragment of FN in the concentration described above. Culture of a cell population in the presence of FN and/or a fragment of FN is disclosed in WO03/080817A, and can be performed with reference to this document. DLL4 for use can also be immobilized on a cell culture carrier in the same manner. If FN and/or a fragment of FN, or DLL4 is immobilized on a solid phase and used, they do not have to be contained in a medium for T cell progenitor differentiation. DLL4 in a medium can be of any concentration as long as T cell progenitors can be produced. For example, the concentration of DLL4 is preferably 0.001 μg/mL to 500 μg/mL, and more preferably 0.01 μg/mL to 500 μg/mL.

The concentration of IL-3 in a medium can be, for example, 0.5 ng/mL to 1000 ng/mL, preferably 1 ng/mL to 500 ng/mL, and more preferably 1 ng/mL to 300 ng/mL.

The medium for T cell progenitor differentiation may also contain, for example, a stem cell factor (SCF), thrombopoietin (TPO), Flt3L (FMS-like tyrosine kinase 3 ligand), IL-6, and/or IL-7 in addition to the ingredients described above.

The medium for T cell progenitor differentiation may contain serum or may be serum-free, and is preferably serum-free.

The medium for T cell progenitor differentiation may also contain a serum alternative (e.g., albumin, transferrin, knockout serum replacement (KSR), fatty acid, insulin, collagen precursor, trace elements, 2-mercaptoethanol, 3'-thiolglycerol, and ITS-supplement). The serum alternatives can be used singly, or in a combination of two or more.

Additionally, the medium for use in the present invention may contain one or more substances of the following: lipids, amino acids (e.g., non-essential amino acids), L-glutamine, vitamins, growth factors, cytokines, antibiotics, antioxidants, pyruvic acid, buffers, inorganic salts, etc.

The medium for T cell progenitor differentiation for use is preferably a chemically-defined medium that does not contain materials with unknown components, such as serum, from the standpoint of reducing the lot-to-lot media variations and of preparing T cell progenitors with stable quality.

The medium for T cell progenitor differentiation has a pH of typically 7.0 to 7.8, and preferably 7.2 to 7.6. The medium is preferably sterilized by a method such as filtration, UV irradiation, heat sterilization, or radiation irradiation before use in order to prevent contamination.

The medium for T cell progenitor differentiation can be prepared in a solution form, a dry form, or a concentrated form (e.g., 2-fold to 1000-fold). The medium in a concentrated form can be diluted to an appropriate concentration for use. The liquid for use in diluting a medium of a dry form or a concentrated form is suitably selected from water, a buffered aqueous solution, a physiological saline solution, and the like.

The present invention further provides a kit for T cell progenitor differentiation. The kit for T cell progenitor differentiation contains the same ingredients as those of the medium for T cell progenitor differentiation. In an embodiment of the present invention, the kit for T cell progenitor differentiation contains an aryl hydrocarbon receptor antagonist, an appropriate solid phase (e.g., a cell culture vessel material, and a cell culture carrier such as beads, membranes, glass slides) on which fibronectin and/or a fragment of fibronectin and DLL4 are immobilized, and IL-3. In an embodiment of the present invention, fibronectin and/or a fragment of fibronectin and DLL4 may be those immobilized on an appropriate solid phase beforehand, or those designed to be immobilized on an appropriate solid phase when used.

The culture in the present invention may be either adhesion culture or suspension culture.

The production method of the present invention is preferably performed in the absence of feeder cells. Because the production method of the present invention enables culture in the absence of feeder cells, the production method enables stable production of T cell progenitors with uniform properties without contamination by materials with unknown components.

In the present specification, the phrase "in the absence of feeder cells" or "feeder-free" basically means not containing feeder cells, and not using a medium preconditioned by culturing feeder cells. Thus, the medium contains no substances such as growth factors and cytokines secreted from feeder cells.

The term "feeder cells" or "feeder" refers to cells that can be co-cultured with cells of different kind, and that provide an environment that supports and allows the cells to grow. Feeder cells may be of the same or different origin as that of the cells the feeder cells support. For example, feeders for human cells for use may be human dermal fibroblasts or human embryonic stem cells, or primary cultures of mouse embryo fibroblasts or immortalized mouse embryo fibroblasts. Feeder cells can be inactivated by exposure to irradiation or mitomycin C treatment.

The culture conditions for the production method of the present invention are not particularly limited. The culture temperature is, for example, about 37 to 42° C., and preferably about 37 to 39° C. The culture period is also not particularly limited and can be suitably determined by a person skilled in the art while monitoring, for example, the number of T cell progenitors. For example, the culture period can be 10 days or longer. The culture in the present invention may include as many times the passage as necessary to obtain a desired amount of T cell progenitors, or may include addition or replacement of the medium. The culture in the present invention can be performed by using a known $CO_2$ incubator.

The $CD34^+$ cells for use in the production method of the present invention are ($CD34^+$) cells that express CD34. In an embodiment, the $CD34^+$ cells are ($CD34^+/CD7^-$) cells that express CD34 and that do not express CD7. In another embodiment, the $CD34^+$ cells are hemogenic endothelial cells (HECs). The hemogenic endothelial cells refer to ($CD34^+/CD43^-/CD184^-/CD73^-$) cells that express CD34, and that do not express CD43, CD184, and CD73 (because $CD34^+/CD43^-/CD184^-/CD73^-$ cells do not express CD7, $CD34^+/CD43^-/CD184^-/CD73^-$ cells are also referred to as $CD34^+/CD7^-/CD43^-/CD184^-/CD73^-$ cells). Thus, the use of hemogenic endothelial cells in step (1) enables the production of T cell progenitors with higher efficiency.

The production method of the present invention may further includes step (X) of preparing iPS cells.

The method for preparing iPS cells can be the methods described above. The prepared iPS cells are induced to be differentiated into $CD34^+$ cells, and the $CD34^+$ cells can be used in the culture of step (1). In the present invention, when pluripotent stem cells other than iPS cells are used, other pluripotent stem cells in place of iPS cells are prepared in step (X).

The production method of the present invention may further includes step (Y) of inducing differentiation of pluripotent stem cells into $CD34^+$ cells.

The differentiated $CD34^+$ cells can be used in culture of step (1). The differentiation of pluripotent stem cells into $CD34^+$ cells can be induced according to a known method. If the pluripotent stem cells are iPS cells, $CD34^+$ cells can be produced, for example, by inducing differentiation of hematopoietic progenitor cells according to the methods disclosed in WO2017/221975, WO2018/135646, or Cell Reports 2 (2012) 1722-1735.

The production method of the present invention may further includes step (Z) of selecting hemogenic endothelial cells ($CD34^+/CD43^-/CD184^-/CD73^-$ cells) from the $CD34^+$ cells obtained in step (Y).

The isolation of hemogenic endothelial cells from $CD34^+$ cells can be performed according to a known method. Examples of such methods include flow cytometry and magnetic cell separation. The use of selected hemogenic endothelial cells in the culture of step (1) enables the production of T cell progenitors with higher efficiency.

The T cell progenitor inducer according to the present invention may contain the same ingredients as those of the medium for T cell progenitor differentiation described above. When used in the production method described above, the medium for T cell progenitor differentiation and the T cell progenitor inducer according to the present invention can induce the differentiation into T cell progenitors.

The production method, medium for T cell progenitor differentiation, and T cell progenitor inducer of the present invention enables the production of T cell progenitors with high efficiency.

The T cell progenitors produced by the production method of the present invention are useful in the treatment of animals (in particular, humans) in need of an increase of the number of T cells. The phase "in need of an increase of the number of T cells" refers to a condition in which the number of T cells in blood is reduced compared with that of healthy animals (e.g., a condition after treatment with an anticancer agent and/or radiotherapy, or a condition with acquired immunodeficiency syndrome (AIDS)). The T cell progenitors produced by the production method of the present invention are also useful in cell therapy, for example, for the recovery of T cells from thymic disorder after radiotherapy. T cell progenitors for use in cell therapy may be T cell progenitors transfected with a desired gene. Such cells can be used to treat genetic disorder (e.g., recombinase deficiency, recombinase regulation gene deficiency, or severe combined immunodeficiency (SCID)). Thus, the present invention provides a pharmaceutical composition containing T cell progenitors produced by the production method described above (in particular, a cell-transplant therapeutic agent) and a cell therapy using the T cell progenitors.

In such a cell therapy, from the standpoint of preventing rejection, the subject from which T cells are isolated preferably has the same HLA type as a subject to which T cell progenitors are administered, and is more preferably the same as the subject to which T cell progenitors are administered.

The pharmaceutical composition according to the present invention can be produced as an oral or parenteral formulation by, for example, mixing an effective amount of T cell progenitors with a pharmaceutically acceptable carrier according to known means. The pharmaceutical composition according to the present invention is usually produced as a parenteral formulation, such as injections, suspensions, and intravenous solutions. Examples of pharmaceutically acceptable carriers include solvents, bases, diluents, excipients, analgesics, buffers, preservatives, stabilizers, suspending agents, isotonic agents, surfactants, and solubilization agents.

The dosage of the pharmaceutical composition according to the present invention can be appropriately determined according to various conditions such as the patient's weight, age, gender, and symptoms. The pharmaceutical composition according to the present invention is applicable to mammals including humans.

EXAMPLES

The present invention is described in more detail below with reference to Examples. However, the present invention is not limited to these Examples.

Example 1: Study with the Method for Producing $CD34^+CD7^+$ T Cell Progenitor The cell population containing hemogenic endothelial cells (HECs) for use was a floating cell population obtained by differentiating iPS cells (Ff-I01s04: derived from peripheral blood mononuclear cells of a healthy individual) provided from the Center for iPS Cell Research and Application, Kyoto University, according to known methods (e.g., the methods disclosed in Cell Reports 2 (2012) 1722-1735, or WO2017/221975).

Specifically, Ff-I01s04 was seeded at $1\times10^6$ cells/well in an ultra-low-attachment 6-well plate (Day 0). The cells were cultured under hypoxic conditions (5% 02) for 4 days in EB medium (StemPro-34 supplemented with 10 μg/ml human insulin, 5.5 μg/ml human transferrin, 5 ng/ml sodium selenite, 2 mM L-glutamine, 45 mM α-monothioglycerol, and 50 μg/ml ascorbic acid 2-phosphate) supplemented with 50 ng/ml BMP4, 50 ng/ml bFGF, 50 ng/ml VEGF, and 2 μM SB431542 (Day 4). Subsequently, culture was further performed in a medium supplemented with 50 ng/ml bFGF, 50 ng/ml VEGF, and 50 ng/ml SCF for 4 days (Day 8), thereby obtaining a cell population containing HECs. The floating cell population containing HECs were stained with the following antibody set.

TABLE 1

| | |
|---|---|
| Anti-CD34 Antibody | Abcam EP/Cy7 |
| Anti-CD43 Antibody | BD BV510 |
| Anti-CD73 Antibody | BD APC |
| Anti-CD184 Antibody | BD BV421 |
| Anti-CD235a Antibody | BioLegend FITC |
| Anti-CD14 Antibody | BioLegend APC/eF780 |

Figure 2:
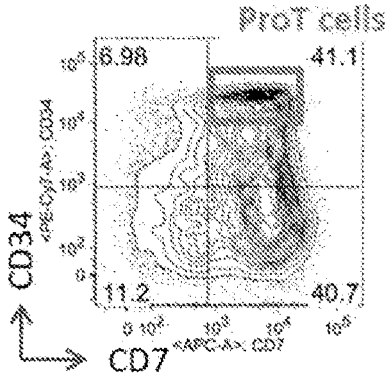
FIG. 2 shows the results of flow cytometry on an immunostained cell population containing T cell progenitors differentiated from induced pluripotent stem cells.

Hemogenic endothelial cells (HECs) induced from iPS cells were sorted by BD FACSAria™ Fusion (FIG. 1) and seeded in an amount of 5,000 per well into a 24-well plate coated with RetroNectin (RN, Takara Bio Inc.) and Fc-tagged recombinant human delta-like 4 (DLL4-Fc, Sino Biological). The plate was prepared in a concentration of 5 μg/ml RN and 5 μg/ml DLL4-Fc. For the culture, StemSpan SFEM II (STEMCELL Technologies) was used as a basal medium. The medium was further supplemented with a 300 ng/ml recombinant human (rh) stem cell factor (SCF, R&D systems), a 300 ng/ml rh FMS-like tyrosine kinase 3 ligand (F1t3L, PeproTech), 100 ng/ml rh thrombopoietin (TPO, PeproTech), 100 ng/ml rh interleukin 7 (IL-7, PeproTech), 100 ng/ml rh interleukin 6 (IL-6, PeproTech), 10 ng/ml rh interleukin 3 (IL-3, PeproTech), and 1 nM StemRegenin 1 (SR1, Calbiochem), followed by culture for 11 days. Halfway through the culture, on day 4 after the start of culture, 500 μl of the medium above was added. On day 7 after the start of culture, a half amount of the medium was replaced. On day 11 after the start of culture, cells were collected with pipetting, and the cell number was measured. The cells were immunostained with the following antibody set, and induction of cells into $CD34^+/CD7^+$ T cell progenitors (proT) was confirmed with a flow cytometer (FACS Aria Fusion, BD Bioscience) (FIG. 2). The cells grew about 150-fold in 10 days of culture, and about 25% of the cells were proT cells.

TABLE 2

| | |
|---|---|
| Anti-CD34 Antibody | Abcam EP/Cy7 |
| Anti-CD45 Antibody | BD BV510 |
| Anti-CD7 Antibody | BioLegend APC |
| Anti-CD4 Antibody | BD BV421 |
| Anti-CD8a Antibody | BioLegend PerCP/Cy5.5 |

Example 2: Assessment of Engraftment Ability of T Cell Progenitor in Thymus

A cell population containing $5\times10^5$ T cell progenitors induced from iPS cells in Example 1 was suspended in 30 μl of an administration liquid (10 μl of D-PBS(−), 10 μl of 250 μg/ml anti-human-mouse IL-7 antibody (M25, Bio X Cell), and 10 μl of 50 μg/ml rhIL-7), and transplanted into the liver of two-day-old neonate NOD.Cg-Prkdc$^{scid}$ Il2rg$^{tmlWjl}$/SzJ (NSG) mice (Charles River Laboratories Japan, Inc.). The thymus was harvested 4 weeks after administration, and whether human CD45-positive blood cells were present was assessed with a flow cytometer.

In the group administered with the cell population, $CD4^+$ $CD8^+$-double-positive cells of human $CD45^+CD3^+$αβTCR+ $CD4^+CD8a^+$ were confirmed.

Figure 3:
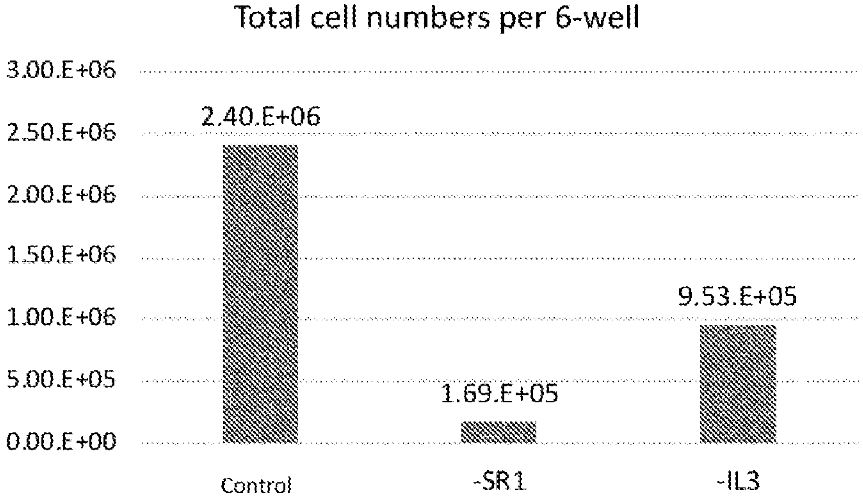
FIG. 3 shows the results of measuring the cell numbers of cell populations containing T cell progenitors differentiated from induced pluripotent stem cells (control condition, a condition in which IL-3 is excluded from the control condition (-IL-3), and a condition in which SR1 is excluded from the control condition (-SR1)).
Figure 4:
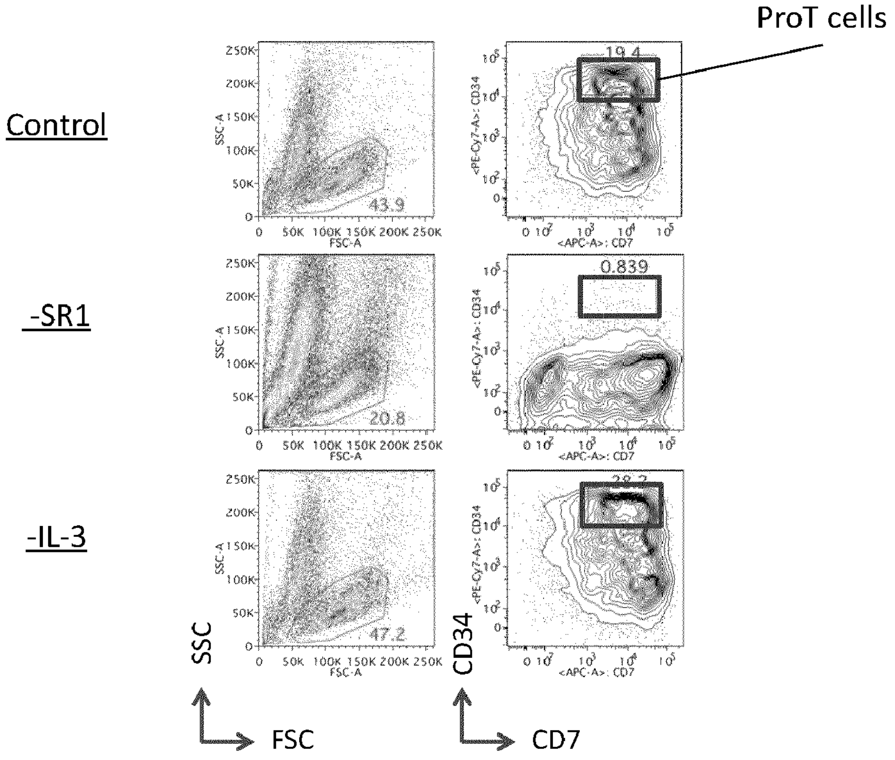
FIG. 4 shows the results of flow cytometry on immunostained cell populations containing T cell progenitors differentiated from induced pluripotent stem cells (control condition, a condition in which IL-3 is excluded from the control condition (-IL-3), and a condition in which SR1 is excluded from the control condition (-SR1)).

Example 3: Assessment of Importance of SR1 and IL-3 in Production of T Cell Progenitor Hemogenic endothelial cells (HECs) derived from iPS cells prepared in the same manner as in Example 1 were sorted by BD FACSAria® Fusion and re-suspended in a StemSpan SFEM II medium, followed by seeding the cells into a culture vessel (6-well plate) coated with RN and DLL4-Fc (225,000/6 wells). The added factors were the following: 300 ng/ml recombinant human (rh) stem cell factor (R&D systems), 300 ng/ml rh FMS-like tyrosine kinase 3 ligand (PeproTech), 100 ng/ml rh thrombopoietin (PeproTech), 100 ng/ml rh interleukin 7 (PeproTech), 100 ng/ml rh interleukin 6 (PeproTech), 10 ng/ml rh interleukin 3 (PeproTech), and 1 nM StemRegenin 1 (SR1, Calbiochem). Three conditions were set: all of these factors were added (control condition), interleukin 3 was excluded from the control condition (-IL-3 condition), and SR1 was excluded from the control condition (-SR1 condition); culture was then performed for 12 days. Halfway through the culture, on day 4 after the start of culture, 500 μl of the medium described above was added. On day 7 after the start of culture, a half amount of the medium was replaced. On day 12 after the start of culture, cells were collected with pipetting, and the cell number was measured. The cells were stained with the antibodies shown in Table 2 and measured with BD FACSAria™ Fusion. The results indicated that cell proliferation was reduced by excluding SR1 or IL-3 from the additives (FIG. 3). Additionally, analysis with a flow cytometer indicated that the added SR1 plays an important role in maintaining the expression level of CD34 (FIG. 4).

The invention claimed is:

1. A method for producing a T cell progenitor, comprising culturing a $CD34^+$ cell in a medium containing an aryl hydrocarbon receptor antagonist and interleukin-3 (IL-3), wherein the $CD34^+$ cell is a $CD34^+/CD43^-/CD184^-/CD73^-$ cell induced from a pluripotent stem cell, wherein the T cell progenitor is capable of engraftment, and wherein the T cell progenitor is obtained from the pluripotent stem cell-derived $CD34^+$ cell.

2. The method according to claim 1, wherein the medium further contains at least one member selected from the group consisting of fibronectin, a fragment of fibronectin, and Delta-like 4 (DLL4).

3. The method according to claim 1, wherein the medium further contains fibronectin and/or a fragment of fibronectin, and DLL4.

4. The method according to claim 1, wherein the aryl hydrocarbon receptor antagonist is StemRegenin 1 (SR1).

5. The method according to claim 1, wherein the culturing is a culture in the absence of a feeder cell.

* * * * *